United States Patent
Mayer

(10) Patent No.: US 8,343,119 B2
(45) Date of Patent: Jan. 1, 2013

(54) STOMA CAP DEVICE FOR OSTOMY MAINTENANCE ASSISTANCE

(76) Inventor: Melanie Juel Mayer, Santa Cruz, CA (US)

( * ) Notice: Subject to any disclaimer, the term of this patent is extended or adjusted under 35 U.S.C. 154(b) by 524 days.

(21) Appl. No.: 12/623,890

(22) Filed: Nov. 23, 2009

(65) Prior Publication Data

US 2010/0145292 A1   Jun. 10, 2010

Related U.S. Application Data

(60) Provisional application No. 61/120,468, filed on Dec. 7, 2008.

(51) Int. Cl.
*A61F 5/44* (2006.01)
(52) U.S. Cl. .................... 604/337; 604/332; 604/338
(58) Field of Classification Search .................. 604/337, 604/332, 338
See application file for complete search history.

(56) References Cited

U.S. PATENT DOCUMENTS

| | | | | |
|---|---|---|---|---|
| 2,437,019 A | * | 3/1948 | Eich | 604/337 |
| 2,448,938 A | * | 9/1948 | Wayne | 604/346 |
| 2,604,092 A | * | 7/1952 | Brown et al. | 128/846 |
| 3,123,074 A | * | 3/1964 | Turner | 604/332 |
| 3,826,242 A | * | 7/1974 | Eggers | 128/898 |
| 5,010,902 A | * | 4/1991 | Rambo et al. | 128/888 |
| 5,908,379 A | | 6/1999 | Schaefer | |
| 6,135,112 A | * | 10/2000 | Harrison et al. | 128/844 |
| 6,569,081 B1 | * | 5/2003 | Nielsen et al. | 600/32 |
| 7,776,028 B2 | * | 8/2010 | Miller et al. | 604/543 |
| 2004/0260257 A1 | | 12/2004 | Ciok | |
| 2008/0269698 A1 | * | 10/2008 | Alexander et al. | 604/332 |

FOREIGN PATENT DOCUMENTS

| | | | | |
|---|---|---|---|---|
| GB | 2014857 A | * | 9/1979 | |
| JP | 2000-116691 A | * | 4/2000 | |
| WO | WO 90/13274 | * | 11/1990 | |

OTHER PUBLICATIONS

International Preliminary Report on Patentability (IPR) for PCT/US2009/066545 published as WO20100065715.*

* cited by examiner

*Primary Examiner* — Tatyana Zalukaeva
*Assistant Examiner* — Ginger T Chapman

(57) ABSTRACT

Provided is a cap device for home use to temporarily cover the stoma resulting from a urostomy, colostomy or ileostomy procedure. It provides a favorable means of preventing leakage during routine cleaning around the stoma during the ostomy pouch replacement process. The device may include, in any combination, use of a flexible elastomeric material for creating low suction to assist with retention, a shaped lip for comfort and sealing, a disposable liner, or internal absorption material to help avoid spillage and leakage.

2 Claims, 3 Drawing Sheets

STOMA CAP DEVICE FOR OSTOMY MAINTENANCE ASSISTANCE

CROSS-REFERENCE TO RELATED APPLICATIONS

This application claims an invention which was disclosed in Provisional Application Number 61120468, filed Dec. 7, 2008, entitled "Stoma Cap Device for Ostomy Maintenance Assistance". The benefit under 35 USC §119(e) of the United States provisional application is hereby claimed, and the aforementioned application is hereby incorporated herein by reference.

REFERENCES CITED

U.S. Pat. No. 3,958,556
U.S. Pat. No. 4,258,704
U.S. Pat. No. 4,950,223
U.S. Pat. No. 5,045,052
U.S. Pat. No. 5,090,424
U.S. Pat. No. 5,125,916
U.S. Pat. No. 6,569,081
U.S. Pat. No. 7,258,661

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The subject matter is in the medical field of devices for home care use. It helps prevent leakage of effluent from the stoma during the cleaning and pouch replacement processes associated with an ostomy. An ostomy procedure is necessary to produce an alternate outlet for waste from the body when the normal path is damaged or must be avoided for medical reasons. This new outlet is a portal constructed of the patient's own body tissue, presenting an opening called a stoma. The stoma typically has a rim approximately one inch in diameter slightly protruding from the abdomen. Being constructed of internal tissue, it is vulnerable to abrasion injury. Normal effluent is collected in a pouch appliance adhesively attached to the skin around the stoma. In some configurations, the pouch may be detachable from a pouch-holder component, called a flange, which is adhesively attached to the skirt. The collection pouch may be emptied multiple times by such detachment or through a valved outlet portion of the pouch.

Periodically, with an interval usually in the 3- to 5-day range, the flange and pouch adhesive interface must be replaced. For appliances with the detachable pouch, such renewal typically involves the following steps:
  Remove the old flange and pouch,
  clean an dry the skin around the stoma where the adhesive interface will contact it,
  apply a new layer of protective skin barrier and allow it to become tacky,
  attach a new adhesive flange to peristoma area, and
  attach a new pouch.

For one-piece pouch appliances, the procedure is similar except for the separate removal and replacement of the flange.

During this replacement process, effluent continues to leak from the stoma and must be collected or prevented from interfering with the tasks. Furthermore, if the peristoma area is not dry when applying the adhesive component, the adhesive will not hold securely, and/or the skin may become irritated and erode with time.

Previous methods to prevent leakage such as those described in U.S. Pat. No. 3,958,556, U.S. Pat. No. 4,258,704, U.S. Pat. No. 4,950,223, U.S. Pat. No. 5,045,052, U.S. Pat. No. 5,090,424, U.S. Pat. No. 5,125,916, U.S. Pat. No. 6,569,081, and U.S. Pat. No. 7,258,661, for instance, involve the less desirable process of inserting something into the stoma.

Other previous methods known to have been suggested by medical professionals to mitigate consequences of leakage include physical obstruction by hand with non-purpose designed objects lacking sealing surfaces, other forms of plugging with penetrating objects, or frequent mechanical wiping, all options with less effectiveness, comfort, or desirability than the current invention.

BRIEF SUMMARY OF THE INVENTION

The subject item, referred to as the Stoma Cap, is a device suitable for temporarily capping a stoma resulting from urostomy, colostomy and ileostomy procedures, to assist in their maintenance processes for short periods during pouch replacement procedures, described in BACKGROUND OF THE INVENTION, by collecting effluent leakage that would interfere with those procedures.

The Stoma Cap provides a method of stopping stoma leakage during cleaning procedures without requiring any penetration of the stoma hole, and it can be left in place through the step of applying the adhesively attached flange, ensuring maintained cleanliness. Some embodiments may facilitate hands-free usage. Further, it is easy to work around the device to perform the procedures described in BACKGROUND OF THE INVENTION. Its smooth opening edge is comfortable and makes a good seal without a lot of pressure. In some embodiments, the Stoma Cap can be applied with a small amount of suction to help keep it in place and make an even better seal. It may be used with hand pressure in cases where vacuum seal is not maintained or desired, and it may be augmented with adhesive or sealing lubricant. It can be loosely packed with absorbent material to absorb the collected effluent and keep it from spilling when the Stoma Cap is removed. It can be easily cleaned after each use, and non-disposable embodiments can be easily sterilized before each use. It can be fitted with a disposable liner to facilitate cleaning. It is inexpensive.

An example embodiment of the Stoma Cap consists of a flexible elastomeric bulb approximately cylindrical in shape with a closed end and an open end. It has a lip around the open end with a comfortably soft rounded flare to encourage it to seal against the skin with minimal force and to avoid contact abrasion and the sort of penetration discomfort a narrow edged hard material might cause. The flexible material also allows the user to squeeze the upper end before application, to encourage formation of a slight vacuum to assist in retaining the device during short intervals such as during cleaning. When a detachable pouch type appliance is used, the narrow size of the Stoma Cap allows installation of the replacement adhesive flange, referred to in BACKGROUND OF THE INVENTION, over the top of the Stoma Cap because the opening in the pouch holder is sized for the stoma and therefore fits over the Stoma Cap which is approximately the same diameter.

Additionally, the Stoma Cap may include internal absorption material such as cotton wadding or cotton balls to collect effluent and help avoid spillage upon removal.

Another embodiment of the Stoma Cap may have multi-segment construction in which each segment is optimized for its function, such as a particularly soft and flexible sealing lip coupled to a firm body for structural support, coupled to a deformable section suitable for squeezing or axial movement useful in creating a vacuum.

Still another embodiment may utilize multiple chambers communicating through check valves such that additional vacuum may be created after attachment to the patient's skin, in order to restore vacuum lost to leakage or influx of gas from the stoma. Such chambers may be within the single piece Stoma Cap device or may be separate and connected through tubing.

Further features of any of the above embodiments may include size adjustment features such as multiple tear-off rings at the open end, each revealing a smaller sealing lip when removed, or a roll-back flexibility which produces a smaller diameter opening as the lip is rolled back due to a substantially conical shape near the open end. Also, the Stoma Cap may be provided in different sizes to fit various stoma diameters.

Another advantageous feature may be construction such that the Stoma Cap is reversible to facilitate internal cleaning.

Still another embodiment may be a Stoma Cap that is a single-use, consumable, disposable element of an ostomy service kit, avoiding the need for cleaning, inserting absorbent material and subsequent handling of contaminated absorbent material, and allowing sterile conditions with every use.

Additionally, adhesive, selected for appropriate removable tackiness and biological inactivity, may be used to assist sealing and retention of the Stoma Cap over the stoma. Such adhesive may be pre-applied to a disposable single-use Stoma Cap device or may be applied prior to use of a multi-use device.

Additionally, lubricant, such as a bio-inert silicone grease or medical lubricant may be applied to the lip of the Stoma Cap or edge of the stoma region to facilitate superior sealing.

An additional embodiment utilizes the external-only feature of the Stoma Cap, but does not require flexible vacuum retention; rather it may be of a substantially firmer construction, may be shorter and contain less volume, and may be held in place only by manual pressure or adhesive lip.

The primary embodiment utilizes a durable non-consumable body along with consumable disposable inserts containing absorbent material and using a formable substantially water-impermeable membrane to line the inside of the durable body, form over the lip, and seal to the user's body. This saves sterilizing the durable body of the Stoma Cap.

An additional embodiment incorporates a double wall such that the vacuum for retention is presented only along the annular ring of the lip contact to skin, avoiding applying any vacuum to the stoma itself.

DETAILED DESCRIPTION OF THE INVENTION

Figure 1:
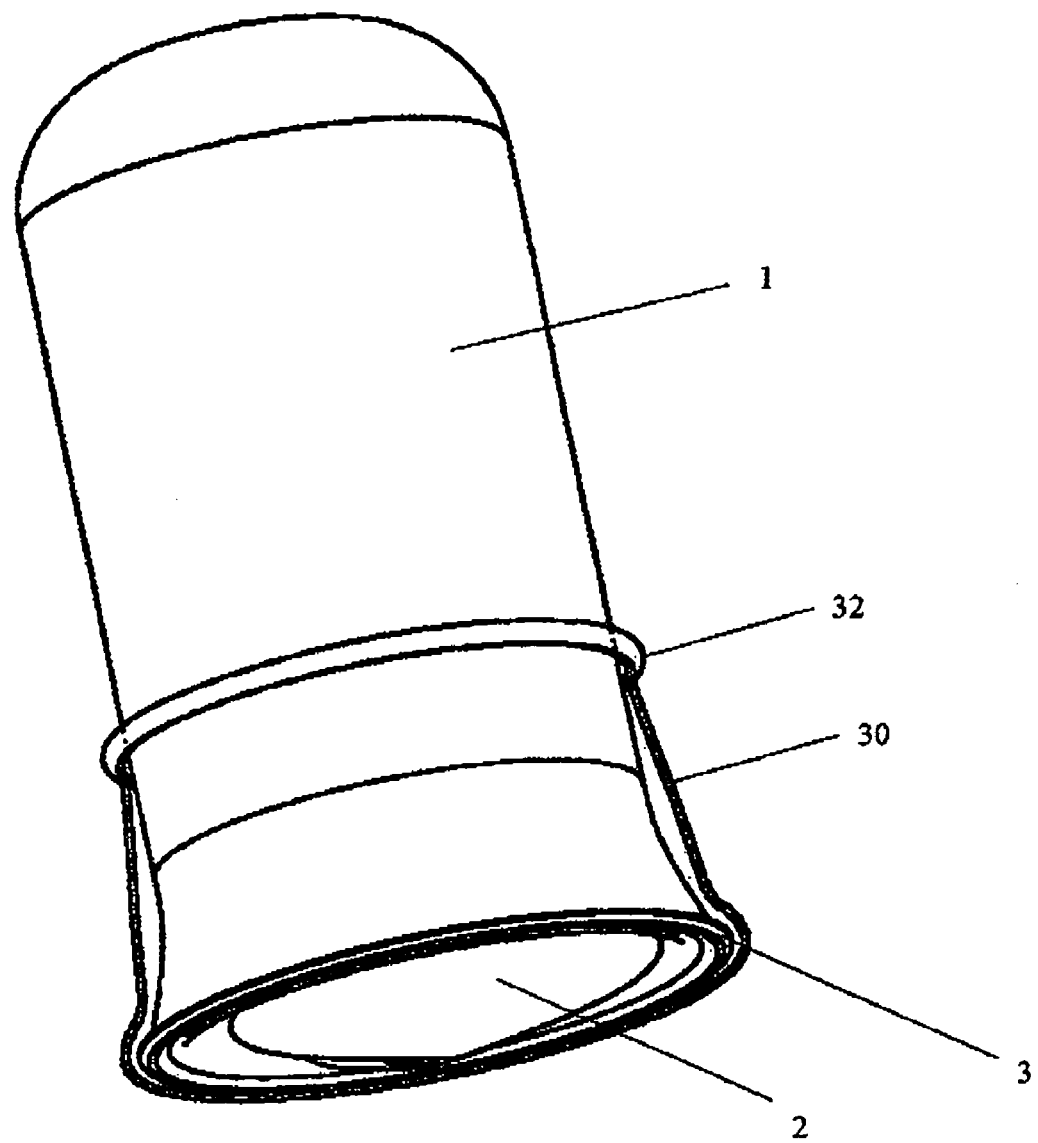
FIG. 1 is an oblique view of the Stoma Cap, shown with an inserted replaceable substantially water-impermeable liner containing absorbent material, the liner folded back over the lip of the Stoma Cap and retained by a strengthened edge.

Referring now to the device in more detail, in FIG. 1 there is shown a Stoma Cap device 1, typically approximately 5 to 7.5 centimeters (2 to 3 inches) long and typically approximately 2.5 centimeters (1 inch) in diameter, although the size may vary to accommodate different sizes of ostomies. It may be fabricated of semi-flexible elastomer such that it can be squeezed by finger pressure but naturally spring back to the shape shown. The lip 3 of the open end of the device is smoothly curved to prevent abrasive edges. The internal cavity has been fitted with a removable substantially water-impermeable liner 30, folded back over Stoma Cap lip 3 and substantially retained by strengthened edge rib 32, discouraging accidental separation from Stoma Cap 1. The internal cavity of the device and liner is shown to contain an amount of absorbent material 2 suitable for absorbing effluent which may leak from the stoma during the use of this device.

Figure 2:
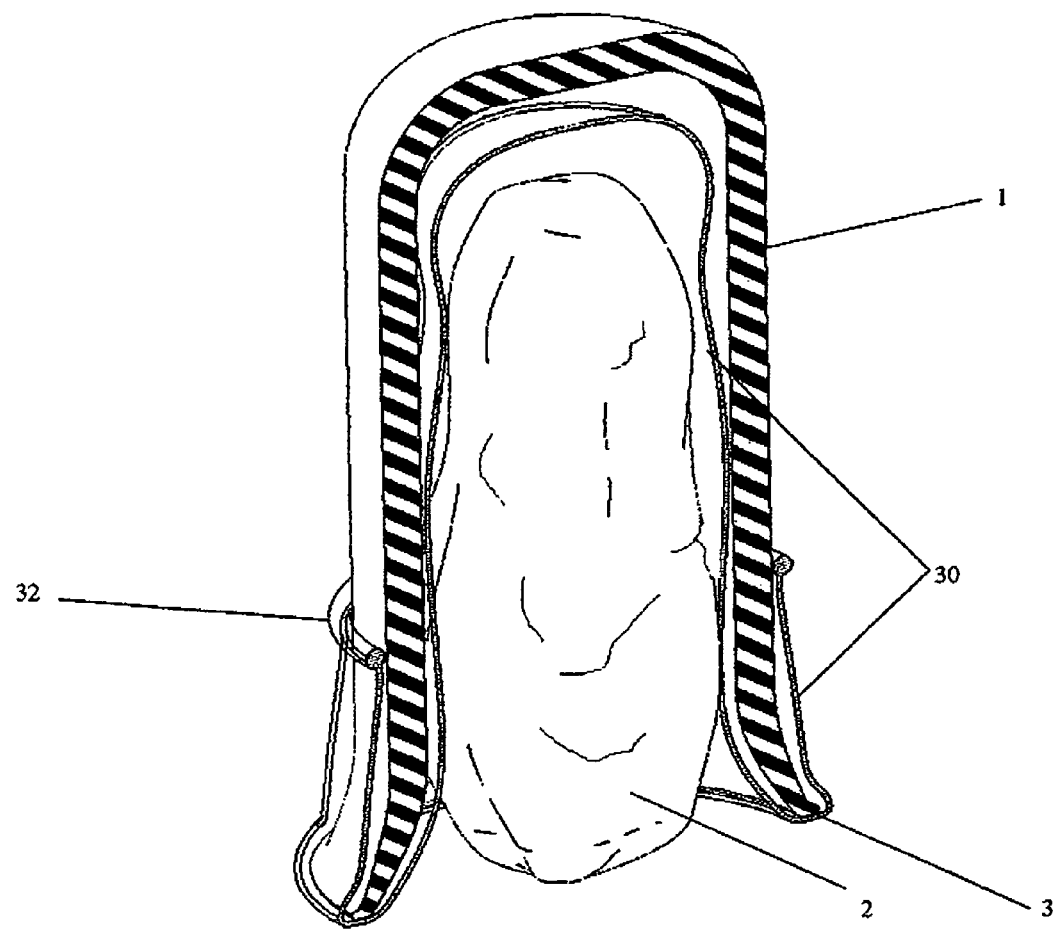
FIG. 2 is a cross section view of the Stoma Cap and liner seen whole in FIG. 1.

Referring now to FIG. 2, there is shown a Stoma Cap device 1, which view is sectioned to reveal the interior, and shows again all the elements described for FIG. 1.

Figure 3:
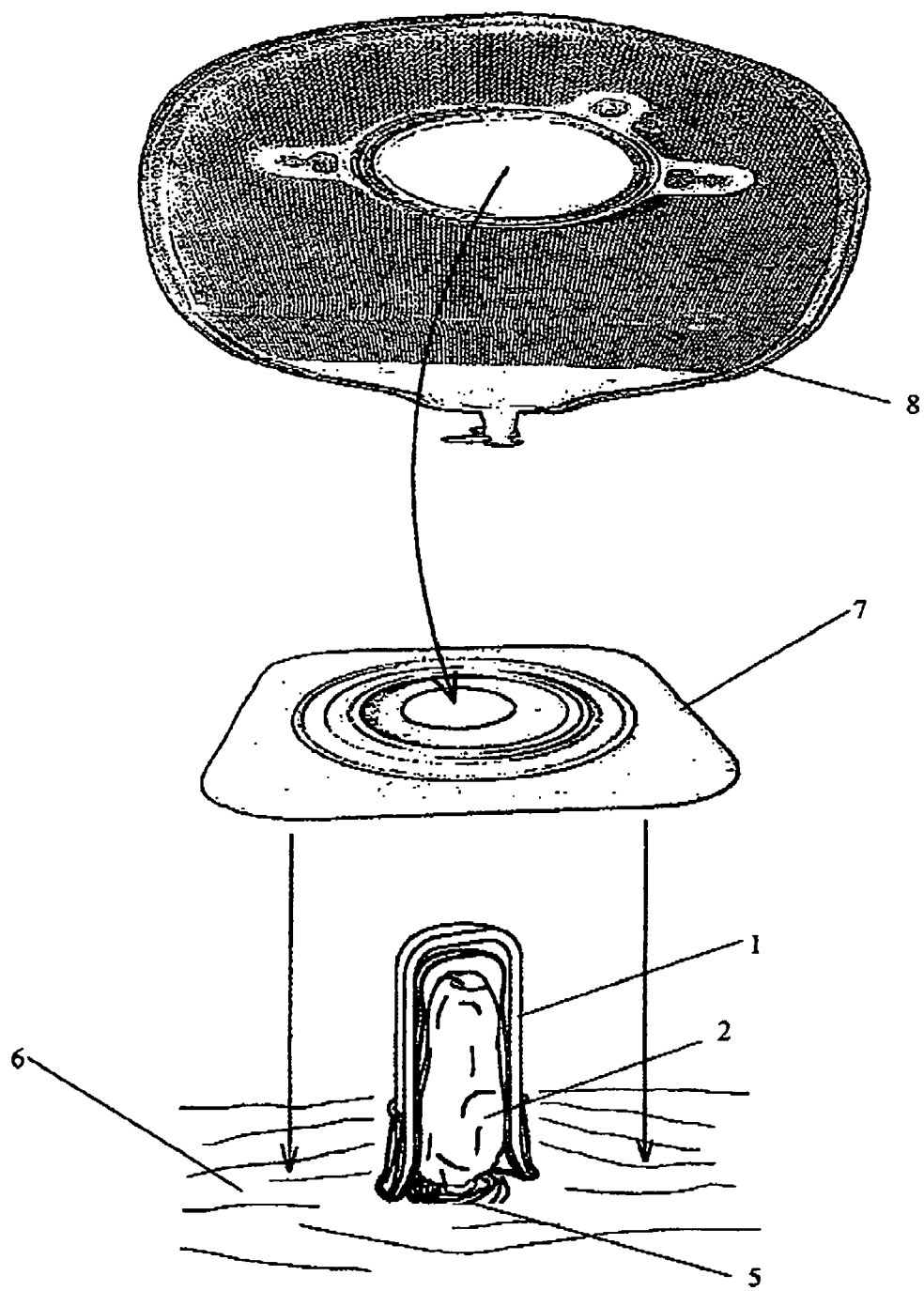
FIG. 3 is a composite perspective view showing how a two-piece ostomy pouch appliance would be sequentially assembled, using the Stoma Cap to maintain cleanliness through the step of attaching the flange to the skin.

Referring now to the device in more detail, in FIG. 3 there is shown a Stoma Cap device 1, which view is sectioned to reveal the interior, in a use position contacting skin 6 surrounding stoma 5 such that leakage from stoma 5 is discouraged from escaping to the surrounding skin 6 during emplacement of flange 7, which can be slipped over Stoma Cap 1 to adhesively attach to skin 6 without allowing leakage. Subsequently, Stoma Cap 1 can be removed, with spillage discouraged by absorbent material 2 retaining effluent which may have come from stoma 5 during the interval of time that Stoma Cap 1 was in place, and pouch 8 can be attached to flange 7.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

I claim:

1. A stoma capping device comprising:
   a body with a closed end and an open end,
   a lip of said open end shaped to encourage forming a seal against an approximately flat surface, said lip of said open end further shaped and smoothed to discourage abrasion to said approximately flat surface,
   an opening in said open end sized to surround a stoma constructed of an ostomy procedure in a skin of a patient,
   an interior volume of said body providing enclosed space suitable for containing a volume of effluent from said stoma, and said interior volume of said body also providing enclosed space suitable for containing an absorbent material,
   a disposable substantially water-impermeable liner which has a closed end inserted substantially into said stoma cap cavity, an open end which may extend beyond the open end of said stoma cap when said closed end is inserted into said stoma cap cavity, and which may have said extended open end folded back over said stoma cap sealing lip so as to protect said stoma cap device from contact with stoma effluent.

2. A stoma capping device as in claim 1 in which said liner has a rolled or strengthened edge to discourage stretching and thereby provide more secure retention to said stoma capping device when folded back over said stoma cap sealing lip.

* * * * *